(12) United States Patent
Aizenberg et al.

(10) Patent No.: US 7,608,446 B2
(45) Date of Patent: Oct. 27, 2009

(54) NANOSTRUCTURED SURFACE FOR MICROPARTICLE ANALYSIS AND MANIPULATION

(75) Inventors: Joanna Aizenberg, New Providence, NJ (US); Paul Kolodner, Hoboken, NJ (US); Thomas Krupenkin, Warren, NJ (US); Joseph Ashley Taylor, Springfield, NJ (US)

(73) Assignee: Alcatel-Lucent USA Inc., Murray Hill, NJ (US)

( * ) Notice: Subject to any disclaimer, the term of this patent is extended or adjusted under 35 U.S.C. 154(b) by 447 days.

(21) Appl. No.: 10/954,552

(22) Filed: Sep. 30, 2004

(65) Prior Publication Data

US 2006/0068487 A1 Mar. 30, 2006

(51) Int. Cl.
*C12M 1/42* (2006.01)
(52) U.S. Cl. ............... 435/285.2; 435/173.1; 435/173.4; 204/164; 204/228.1; 422/50; 422/68.1
(58) Field of Classification Search ............... 435/173.1, 435/173.4; 204/164, 228.1
See application file for complete search history.

(56) References Cited

U.S. PATENT DOCUMENTS

| | | | |
|---|---|---|---|
| 5,457,041 A * | 10/1995 | Ginaven et al. ............ 435/455 |
| 6,100,084 A | 8/2000 | Miles et al. | |
| 6,645,757 B1 * | 11/2003 | Okandan et al. ......... 435/285.1 |
| 6,783,647 B2 | 8/2004 | Culbertson et al. | |
| 7,048,889 B2 * | 5/2006 | Arney et al. ............... 422/68.1 |
| 7,067,328 B2 * | 6/2006 | Dubrow et al. ............... 438/1 |
| 2002/0185557 A1 | 12/2002 | Sparks | |
| 2003/0186430 A1 | 10/2003 | Tai et al. | |
| 2004/0182707 A1 * | 9/2004 | Jardemark et al. .......... 204/451 |

FOREIGN PATENT DOCUMENTS

| | | |
|---|---|---|
| EP | 1584375 | 10/2005 |
| WO | WO 9925816 | 5/1999 |
| WO | WO 03037781 | 5/2003 |
| WO | WO 03055976 | 7/2003 |
| WO | WO 2004021083 | 3/2004 |

OTHER PUBLICATIONS

Michael Pycraft Hughes, "AC Electrokinetics: Applications for Nanotechnology," The Seventh Foresight Conference on Molecular Nanotechnology, Oct. 15-19, 1999, pp. 1-15.
Tsung Chain Chang, et al., "Rapid Differentiation of Fermentative from Nonfermentative Gram-Negative Bacilli in Positive Blood Cultures by an Impedance Method," Aug. 2000, 6 pages, Journal of Clinical Microbiology, Oct. 2000, vol. 38, No. 10, pp. 3589-3594.

(Continued)

*Primary Examiner*—N. Yang
(74) *Attorney, Agent, or Firm*—Hitt Gaines, PC

(57) ABSTRACT

The present invention provides an apparatus, comprising a first mechanical structure having a first rigid surface, an area of the first rigid surface having a nanostructured surface. The apparatus also includes a second mechanical structure having a second rigid surface and opposing the first mechanical structure. The second rigid surface is cooperable with the nanostructured surface such that a microscopic particle is locatable between the nanostructured surface and the second rigid surface.

25 Claims, 10 Drawing Sheets

OTHER PUBLICATIONS

U.S. Appl. No. 10/649,285, filed Mar. 31, 2003, Method and Apparatus for Conrolling Friction Between a Fluid and a Body, 25 pages.

U.S. Appl. No. 10/403,159, filed Aug. 27, 2003, entitled "Method and Apparatus for Controlling the Movement of a Liquid on a Nanostructured or Microstructured Surface," Kornblit, et al., currently pending, 44 pages.

Tom N. Krupenkin, et al., "The Dynamic Tuning of Liquids on Nanostructured Surfaces," ACS Publications, http://pubs3.acs.org/acs/journals/doilookup7in_dol=10.1021/la036093q, American Chem. Society, 2004. 14 pages.

J. Bhardwaj, et al, "Advances in High Rate Silicon and Oxide Etching using ICP," presented at the MEM/MST Technology Symposium at Semicon West, 1999, 6 pages.

Di Carlo, et al., "Mechanical Cell Lysis Results of a Sample Preparation Module for Functional Genomics", Annual International IEEE-EMBS Special Topic Conference on Microtechnologies in Medicine and Biology Proceedings, May 2, 2002, pp. 527-530.

\* cited by examiner

NANOSTRUCTURED SURFACE FOR MICROPARTICLE ANALYSIS AND MANIPULATION

TECHNICAL FIELD OF THE INVENTION

The present invention is directed, in general, to an apparatus and methods for testing and rupturing microparticles.

BACKGROUND OF THE INVENTION

In many biological applications, it is desirable to rupture microparticles so that their contents can be analyzed, or to identify or characterize intact microparticles. For instance, there is great interest in the development of cost effective and rapid methods for monitoring the presence and concentration of bacterial or other cells in military, medical, agricultural and food preparation applications. The analysis of cells often requires that they be ruptured, so that the contents of the cells can be analyzed. For certain microparticle types, however, rupturing is problematic.

For instance, when stressed or starved for nutrients, vegetative bacterial cells can differentiate into dormant endospores, more commonly referred to as spores. Spores are highly resistant to inactivation and rupture by various physical treatments, including mechanical agitation, ultraviolet and gamma radiation, heat, and chemical treatments. The need for bulky complex equipment, such as microwave or ultrasonic instrumentation, to accomplish rupturing, adds significantly to the cost, and decreases the speed, of detecting and analyzing such cells. In addition, the harsh conditions presently used for rupturing can inadvertently damage the contents of the cells. For example, rupture via the chemical action of surfactants, or the physical stress provided by sonication, can damage or denature DNA, protein, or other components in the cell. Similar concerns exist for the analysis of non-biological microparticles.

The present invention overcomes these problems by providing an apparatus that uses nanostructured surfaces to facilitate the rupture or testing of microparticles, as well as methods of using and making such an apparatus.

SUMMARY OF THE INVENTION

To address the above-discussed deficiencies, one embodiment of the present invention provides an apparatus comprising a first and a second mechanical structure. The first mechanical structure has a first rigid surface. An area of the first rigid surface has a nanostructured surface. The second mechanical structure has a second rigid surface. The second rigid surface opposes the first mechanical structure and is cooperable with the nanostructured surface such that a microscopic particle is locatable between the nanostructured surface and the second rigid surface.

Another embodiment of the invention is a method of use. The method includes placing a plurality of microscopic particles in an embodiment of the above-described apparatus and applying a force to the plurality of microscopic particles using the nanostructured surface and the second rigid surface.

Yet another embodiment of the present invention is a method of manufacturing an apparatus. The method of manufacture includes forming a first mechanical structure having a first rigid surface and forming a nanostructure in an area of the first rigid surface. The method of manufacture also includes forming a second mechanical structure having a second rigid surface. The second mechanical structure is positioned so that the second rigid surface opposes the first mechanical structure and is cooperable with the nanostructure such that the surfaces apply a force to microscopic particles locatable between the nanostructure and the second rigid surface.

BRIEF DESCRIPTION OF THE DRAWINGS

The invention is best understood from the following detailed description, when read with the accompanying FIGURES. Various features may not be drawn to scale and may be arbitrarily increased or reduced for clarity of discussion. Reference is now made to the following descriptions taken in conjunction with the accompanying drawings, in which.

DETAILED DESCRIPTION

The present invention recognizes the advantageous use of nanostructures to facilitate the testing or rupture of microparticles. Nanostructured surfaces are desirable because they provide a small area of contact and, therefore, promote the development of high stresses at a nanostructure-microparticle surface. The term nanostructured surface as used herein is defined as a surface having an array of protruding structures, each structure having lateral dimensions ranging from about 50 nanometers to about 1000 nanometers. Nanostructured surfaces can be advantageously used to rupture a microparticle with a minimum of damage to its contents, as compared to conventional rupturing techniques that use regular unstructured surfaces. Nanostructures can also be advantageously used to facilitate the collection of information about the microparticle. Such information can include measuring of the elastic properties of microparticles, determining when a microparticle has been ruptured, or establishing the identity of a microparticle.

Figure 1:
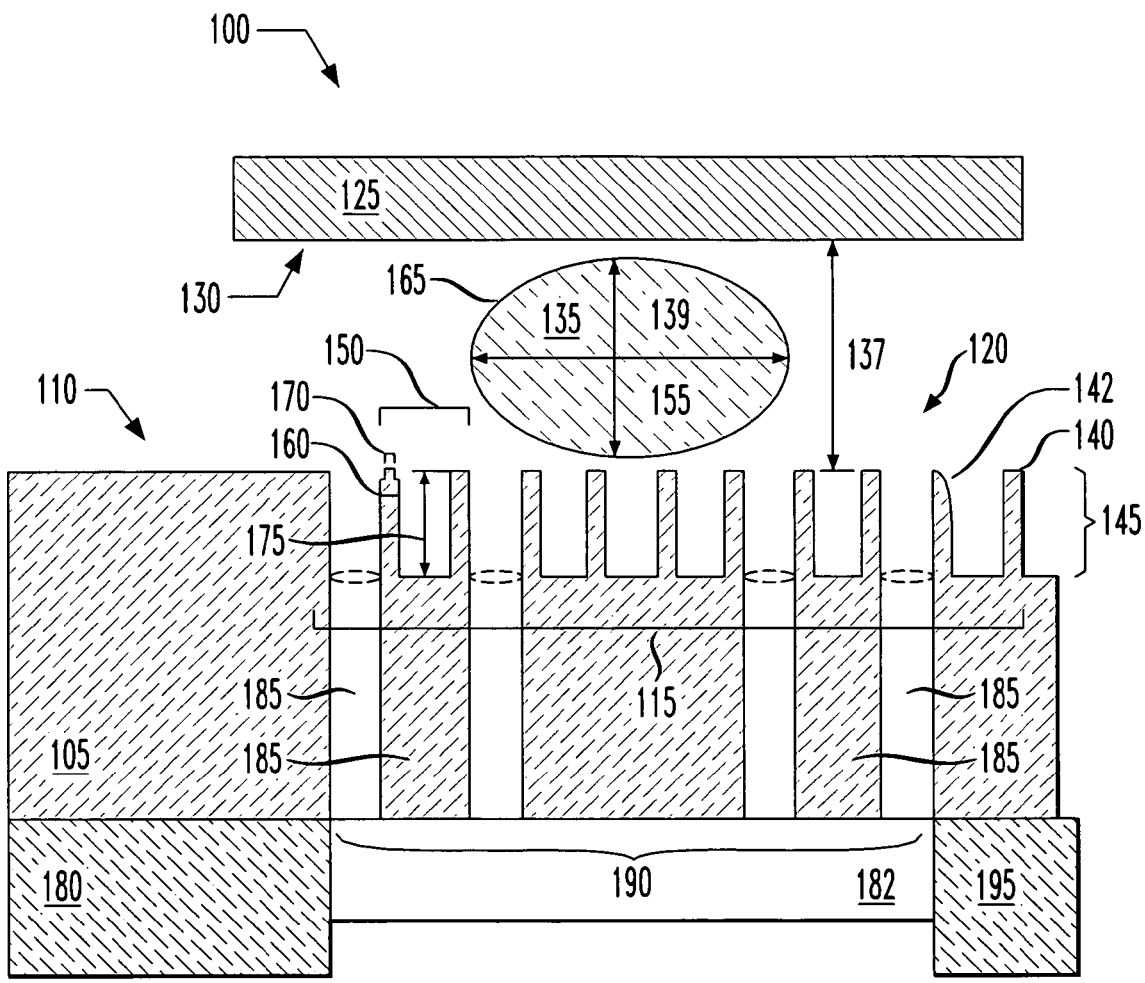
FIG. 1 illustrates a cross-sectional view of an exemplary apparatus for applying a contact force to a microparticle.

FIG. 1 illustrates a cross sectional view of a portion of an exemplary apparatus 100 for applying a contact force to a microparticle. The apparatus 100 comprises a first mechanical structure 105 having a first rigid surface 110. An area 115 of the first rigid surface 110 has a nanostructured surface 120. The apparatus 100 further includes a second mechanical structure 125 having a second rigid surface 130. The second rigid surface 130 opposes the first mechanical structure 105 and is cooperable with the nanostructured surface 120 such that a microscopic particle 135 is locatable between the nanostructured surface 120 and the second rigid surface 130.

One of ordinary skill in the art would appreciate that there are numerous ways that the nanostructured surface 120 and the second rigid surface 130 can cooperate to locate the microparticle 135 between the second rigid surface 130 and the nanostructured surface 120. In the exemplary apparatus 100 shown in FIG. 1, the second rigid surface 130 is positioned a distance 137 over the nanostructured surface 120 such that the microscopic particle 135 can be located between the nanostructured surface 120 and the second rigid surface 130. The distance 137 between the nanostructured surface 120 and the second rigid surface 130 can be adjusted to help retain the microscopic particle 135 between these surfaces 120, 130. For instance, in some cases, the distance 137 is less than about twice an average diameter 139 of the microparticle 135.

The nanostructured surface 120 can be made by dry etching the surface 110 of the first mechanical structure 105 using procedures well known to those skilled in the art. The first and second mechanical structures 105, 125 can comprise a first and second semiconductor substrate, respectively, such as silicon wafers. In some instances, it is advantageous for the second rigid surface 130 to also have a nanostructured surface.

FIG. 1 shows a preferred nanostructured surface 120 that comprises pins 140. The term pin is used herein to refer to structures having variety of shapes, including cylindrical, square, triangular, prisms, pyramids, rectangular-shaped structures or combinations thereof. In some cases, for instance, the nanostructured surface 120 can have blades 142, such as unidirectional blades, configured to rupture the microparticle 135. In some cases, it is advantageous to arrange the pins 140 into a one-dimensional array to form a saw or a two-dimensional array to form grass-shaped structures. For instance, FIG. 1 shows a cross-sectional view of a nanostructured surface 120 comprising nanograss 145.

The microparticle 135 can comprise biological cells, including plant, animal or bacterial cells. In some cases, the microparticle 135 is a bacterial spore, such as *Bacillus anthracis, subtilis*, or *thuringiensis*. Alternatively, the microparticle 135 can comprise a nonbiological particle, such as a microsphere. Some preferred microspheres comprise a latex sphere holding chemicals inside the sphere. In some embodiments of the apparatus 100, more than one microparticle 135 can be located between the nanostructured surface 120 and the second rigid surface 130.

In the embodiment depicted in FIG. 1, one or both of the first rigid surface 110 and the second rigid surface 130 are movable with respect to each other and can thereby cooperate to apply a contact force to the microscopic particle 135 through the nanostructured surface 120. Certain desirable embodiments of the nanostructured surface 120 help to ensure that the nanostructured surface 120 contacts the microparticle 135. Advantageous nanostructured surfaces 120 can include pins 140 configured to have a pitch 150 that is smaller than about one-half of an average diameter 155 of the microscopic particle 135. In some cases, the pin 140 has a diameter 160 that is less than about one tenth of the average diameter 155 of the microparticle 135.

It is desirable for the first and said second rigid surfaces 110, 130 to be substantially planar because this helps ensure that the contact force is applied in a well-controlled manner, regardless of the microparticle's 135 location between the nanostructured surface 120 and the second rigid surface 130. In addition, positioning the first and said second rigid surfaces 110, 130 to be substantially parallel to each other helps to hold the microparticle 135 between the nanostructured surface 120 and the second rigid surface 130 while the contact force is applied. In other cases, however, one or both of the first and said second rigid surfaces 110, 130 can have convex, concave, or other shapes.

When the contact force is designed to rupture the microparticle 135, it is desirable for the pin's diameter 160 to be configured to facilitate lysing of a membrane or coating 165 of the microparticle 135. In some cases, the diameter 160 is less than about 1 micrometer, and more preferably less than about 400 nanometers. It is sometimes desirable for the pins 140 to have a narrowed or pointed tip, because this facilitates a highly localized force being applied to the microparticle 135, resulting in efficient rupture of its membrane or coat 165. In some cases, the tip diameter 170 is one-half to one-tenth of the pin diameter 160.

In other cases, the contact force is designed to gather information about the microparticle 135, such as the microparticle's 135 elastic properties. For instance, applying an incrementally increasing contact force to the microparticle 135 allows the compressibility of the microparticle 135 to be assessed. A measurement of compressibility can be used to identify the state of the microparticle 135, e.g., vegetative versus active bacterial cells. In such applications, to avoid rupturing the microparticle 135, it can be desirable for the tip diameter 170 to be about the same length as the pin diameter 160.

As shown in FIG. 1, both the pin pitch 150 and height 175 can be uniform throughout the area 115 comprising the nanostructured surface 120. In some preferred embodiments of the apparatus 100, the pitch 150 ranges from about 0.5 to about 5 micrometers. In some cases, however, it is advantageous for the pitch 150 throughout the area 115 to be nonuniform, because this permits a contact force to be applied to differently sized microparticles 135. A nonuniform pitch 150 can also facilitate the application of different forces to same-size microparticles 135 positioned at different locations in the area 115. A nonuniform pitch 150 can also help retain the microparticle 135 between the nanostructure surface 120 and second rigid surface 130. For similarly reasons discussed above, it can be beneficial for the height 175 of the pins 140 to be nonuniform. In some cases, the height 175 ranges from about 1 micrometer to 7 micrometers.

As further illustrated in FIG. 1, some embodiments of the apparatus 100 further comprise a system 180 configured to analyze material released from the microparticle 135 when it is ruptured. Non-limiting examples of the system 180 include machines to conduct immunological or nucleic acid assays, chromatographic and spectroscopic analysis, or combinations thereof. In some embodiments, the system 180 is coupled to the apparatus 100 via a channel 182, such as a microfluidic channel, that directs materials or chemicals released from the microparticle 135 to the system 180. It can be advantageous for the one or both of the first rigid surface 110 or the second rigid surface 130 to further comprise openings 185 to form a permeable membrane 190. In the embodiment shown in FIG. 1, the area 115 of the first rigid surface 110 comprises the openings 185.

The apparatus 100 can further comprise a device 195, such as a pump or other hydraulic machine, configured to pass material released from the microparticle 135 through the openings 185. For instance, the device 195 can facilitate passage by irrigating supplemental material across the permeable membrane 190, including a chemically reactive substance such as a detergent or denaturant, or a liquid, such as water.

Figure 2:
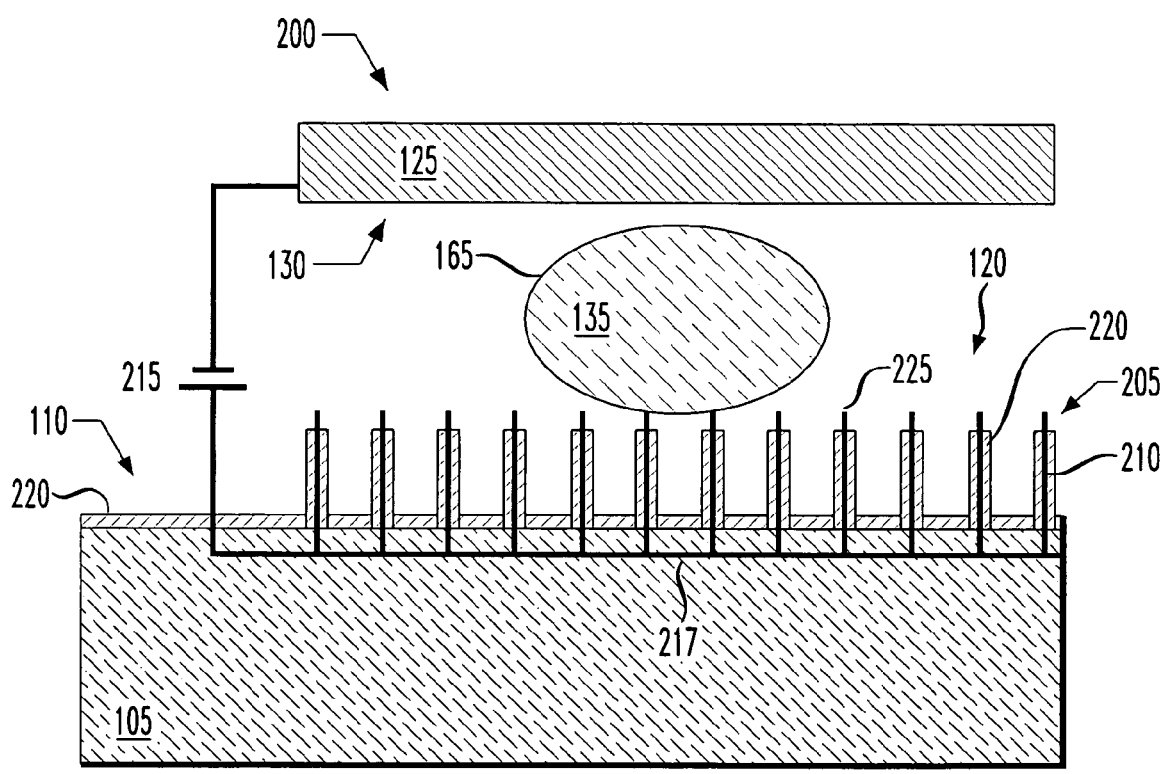
FIG. 2 illustrates a cross-sectional view of a second exemplary apparatus for applying an electric current to a microparticle.

FIG. 2 illustrates a cross-sectional view of a second exemplary apparatus 200 for applying an electric current to a microparticle 135. Elements of the apparatus 200 that are analogous to the apparatus shown in FIG. 1 are assigned the same reference number. The first rigid surface 110 and the second rigid surface 130 of the apparatus 200 can cooperate to apply a force comprising an electromagnetic force to the microscopic particle 135 through the nanostructured surface 120. For instance, passing an electric current through the pins 205 and to the surface 165 of the microparticle 135 generates an electromagnetic force on the microparticle 135.

In preferred embodiments of the apparatus 200, such as shown in FIG. 2, the nanostructured surface 120 comprises pins 205 having a conductive core 210. The conductive core 210 and the second rigid surface 130 are electrically coupled to a voltage source 215. As shown in FIG. 2, a plurality of conductive cores 210 can be electrically coupled to each other via one or more conductive lines 217 in the first mechanical structure 105. The conductive core 210 and line 217 can comprise doped silicon. The conductive core 210 and the second rigid surface 130 are configured to transmit an electrical current to the microparticle 135 when the voltage source 215 applies a voltage potential between the conductive cores 210 and the second rigid surface 130.

The strength of current passed to the microparticle 135 can be varied by applying different voltages as appropriate, either to gather information about the microparticle's 135 properties, or to rupture the microparticle 135. Low voltages (e.g., less than about 1 Volt) can be used to generate sufficient current through the conductive core 210 of the pins 205 to produce extremely high, localized power dissipation. This, in turn, causes thermal damage or electrical breakdown, which in turn, can rupture the microparticle's membrane or coat 165.

Still lower voltages (e.g. less than about 0.1 Volts) can be used to measure the microparticle's 135 electrical properties. The identification of different species of cells by measuring their electrical properties such as their capacitance, impedance or conductance, is well known to one of ordinary skill in the art. See e.g., T C Chang and A H Huang, Journal of Clinical Microbiology, October 2000, p. 3589-3594, Vol. 38, No. 10, incorporated by reference herein in its entirety. In some embodiments of the apparatus 200, to measure electrical impedance, a current is passed from the conductive core 210 through the microparticle 135 and to the second rigid surface 130. The electrical impedance of the microparticle 135 can differ depending on its identity, e.g., different electrical impedance for different types of bacteria. The electrical impedance of the microparticle 135 can also differ depending on whether or not the microparticle 135 has ruptured, or depending on the state of the microparticle 135, e.g., vegetative versus active bacterial cells. For example, rupturing a microparticle 135 can cause its contents, e.g., cytoplasm, to spill out into the surrounding fluid, increasing conductivity and causing a detectable change in electrical impedance.

Those skilled in the art are familiar with the procedures used to fabricate pins 205 having a conductive core 210, for example, by dry etching a doped silicon substrate. In some cases, as shown in FIG. 2, the pins 205 further include an insulating layer 220, and only the tip 225 of the conductive core 210 is uninsulated. Such an arrangement can advantageously pass a larger current to the microparticle 135, for a given voltage potential, than using an uninsulated conductive core 210. The procedures to make the insulating layer 220 are also well known to those skilled in the art. For instance, the insulating layer 220 can comprise silicon dioxide conformally grown around the conductive core 210 by a conventional thermal oxidation process, and the conductive tip 225 exposed by a conventional etch process.

Figure 3:
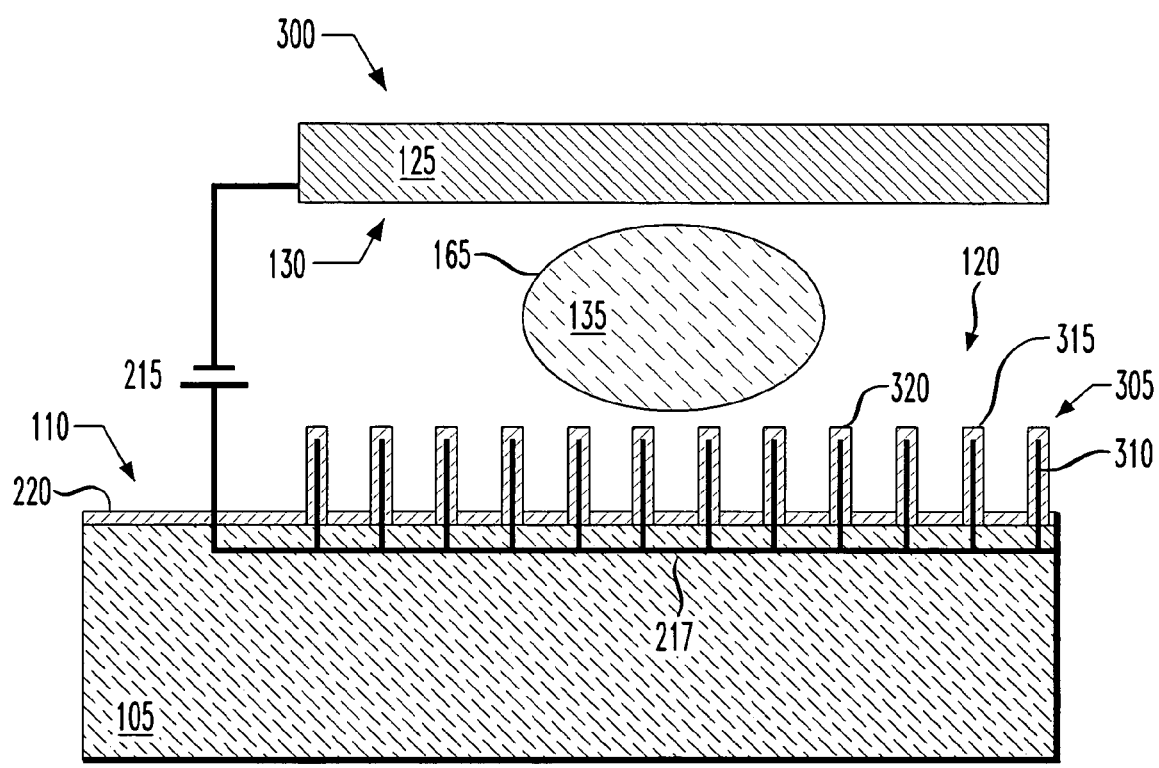
FIG. 3 illustrates a cross-sectional view of a third exemplary apparatus for applying an electric field to a microparticle.

FIG. 3 illustrates a cross-sectional view of a third exemplary apparatus 300 for applying an electric field to a microparticle 135. Elements of the apparatus 300 that are analogous to the apparatuses shown in FIGS. 1 and 2 are given the same reference number. The first rigid surface 110 and the second rigid surface 130 of the apparatus 300 can cooperate to apply a force comprising an electrical force to the microscopic particle 135 through the nanostructured surface 120.

Similar to the apparatus presented in FIG. 2, preferred embodiments of the apparatus 300 comprise pins 305 having a conductive core 310 covered with an insulating layer 315. The conductive core 310 and the second rigid surface 130 are electrically coupled to a voltage source 215. The conductive core 310 and the second rigid surface 130 are configured to apply an electrical field to the microparticle 135 when the voltage source 215 applies a voltage between the conductive core 310 and the second rigid surface 130. For instance, applying a voltage can produce a high, localized electric field at the tip 320 of the pin 305 that can be used to gather information about the properties of the microparticle 135, or to rupture the microparticle 135.

One of ordinary skill in the art would be familiar with the various electrokinetic techniques, such as dielectrophoresis and electrorotation, to manipulate, separate or rupture microparticles 135. See e.g., M. P. Hughes, AC Electrokinetics: Applications for Nanotechnology, in The Seventh Foresight Conference on Molecular Nanotechnology, Oct. 15-17, 1999, Santa Clara, Calif.; and U.S. Patent Application No. 2003/0186430, both incorporated by reference herein in their entirety. For instance, if a dielectric microparticle 135, such as a cell, is exposed to an external electric field it will polarize. The size and direction of the induced dipole will depend on the field frequency and dielectric properties of the microparticle 135 (e.g., its conductivity and permittivity). An inhomogeneous field will cause the electrical force due to the interaction of induced dipole and external field.

Figure 4:
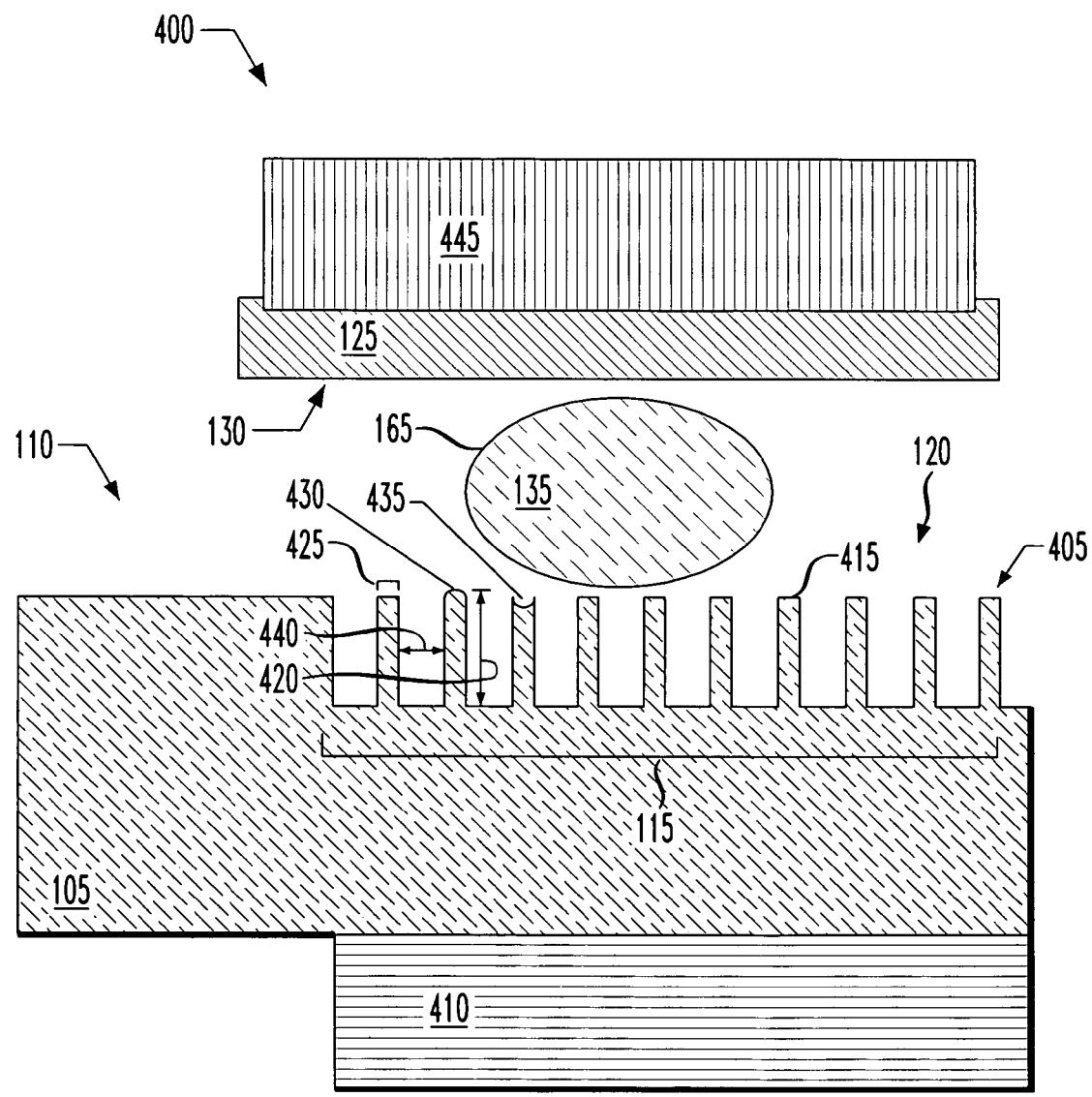
FIG. 4 illustrates a cross-sectional view of a fourth exemplary apparatus for applying an acoustic wave to a microparticle.

FIG. 4 illustrates a cross-sectional view of a fourth exemplary apparatus 400 for applying an acoustic wave to a microparticle 135. Elements of the apparatus 400 that are analogous to the apparatus shown in FIG. 1 are given the same reference number. The first rigid surface 110 and the second rigid surface 130 of the apparatus 400 can cooperate to apply a force comprising an acoustic wave to the microscopic particle 135 through the nanostructured surface 120.

Similar to the apparatus 100 presented in FIG. 1, preferred embodiments of the apparatus 400 comprise pins 405. The pins 405 can have any of the structures or shapes, or combinations thereof, discussed above and shown in FIGS. 1-3. The apparatus 400 further includes a device 410 configured to generate an acoustic wave that is passed to at least one of the first or second rigid surfaces 110, 130. In some cases, the device 410 comprises a piezoelectric material and, as shown in FIG. 4, is coupled to the first rigid surface 110 adjacent to the area 115 of the first mechanical structure 105 where the nanostructured surface 120 is located. In some embodiments of the apparatus 400, the piezoelectric material is configured to apply an ultrasonic wave to the pins 405.

An oscillatory potential applied to the piezoelectric material of the device 410 causes an acoustic force to be transferred from the pins 405 to the microparticle 135. The acoustic force can be used to rupture, or alternatively, gather information about the microparticle 135. Certain wavelengths of the ultrasonic wave cooperate with the pins 405 to alter the acoustic force by inducing diffraction and interference effects to the ultrasonic waves as they propagate through the pins 405. This, in turn, can produce a focusing effect on the acoustic force at the tips 415 of the pins 405. For instance, an acoustic wave can travel down the longitudinal axis 420 of the pins 405 and come out at the tips 415. Acoustic waves having a wavelength comparable to the diameter 425 of the pins 405 are contained inside the pins 405, resulting in a more focused acoustic force emanating from the tips 415. In some instances, a greater focusing of the acoustic force is achieved by providing pins 420 with a hemispherical tip 430 or conical tip 435. In some cases, additional focusing of the acoustic force is achieved by providing acoustic waves having a wavelength comparable to the lateral spacing 440 between pins 405.

In certain embodiments of the apparatus 400 one or more transducers 445 collect reflected or refracted acoustic waves for analysis. For instance, measuring acoustic impedance, the product of the microparticle's sound speed multiplied by the microparticle's density, can establish whether or not the microparticle 135 has ruptured. Similarly, the acoustic impedance of the microparticle 135 can be used to establish its state, e.g., vegetative versus active bacterial cells, or identity, e.g., a particular species of bacterial cell.

For clarity, various aspects of the above apparatuses have been discussed separately and presented in FIGS. 1-4. An apparatus of the present invention, however, could include all or some of the above-described nanostructured surfaces, including pins, and other components, such as the system 180, openings 185, membrane 190 and device 195 discussed in the context of FIG. 1. As an example, with continuing reference to FIGS. 1 and 4, the area 115 can comprise pins 140, 405 are configured to rupture the microparticle 135 from the application of either or both a contact force and an acoustic force through the nanostructured surface 120. Apparatuses that provide other combinations of mechanical, electric current, electric field and acoustic forces as well as solvents delivered through the openings 185 would be readily apparent to one of ordinary skill in the art. Similarly, the above-mentioned combinations of various forces can be used not only to accomplish rupture of the microparticle 135, but also to analyze its physical properties (mechanical, electrical, etc . . . ) either simultaneously with the rupture process or in a separate process.

Figure 5:
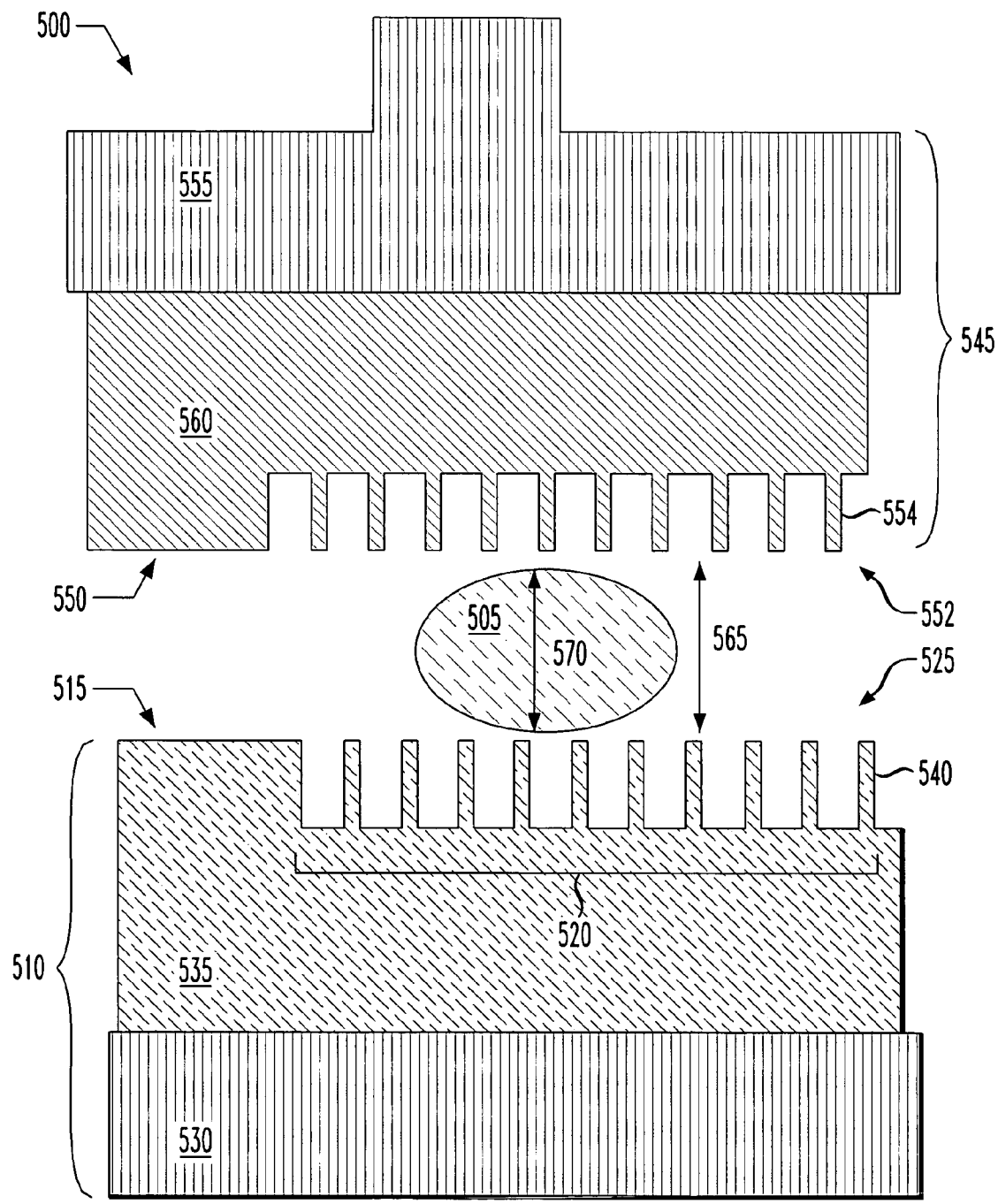
FIGS. 5-6 illustrate cross-sectional views of an exemplary apparatus at selected stages in a method to rupture a microparticle.
Figure 6:
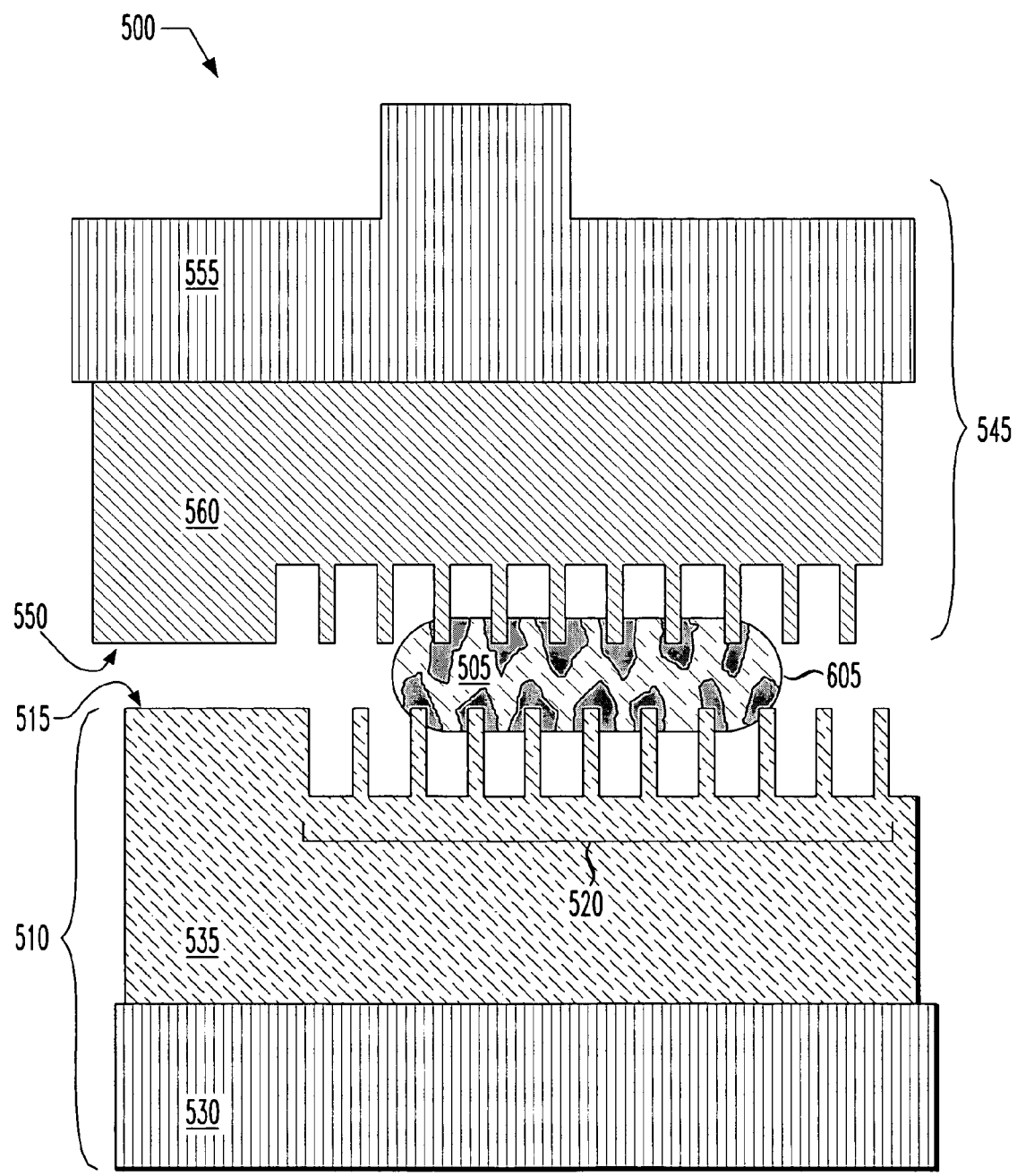

Another embodiment of the present invention is a method of use. FIGS. 5-6 illustrate cross-sectional views of an exemplary apparatus at selected stages in a method to rupture a microparticle. Turning first to FIG. 5, illustrated is the apparatus 500 after placing a microparticle 505 in the apparatus 500. The apparatus 500 can comprise any of the embodiments discussed above and shown in FIGS. 1-4. As illustrated in FIG. 5, a first mechanical structure 510 has a first rigid surface 515, with an area 520 of the first rigid surface 515 having a nanostructured surface 525. As further shown in FIG. 5, in some instances, the first mechanical structure 510 comprises a fixed stage 530 having a silicon substrate 535 thereon. The area 520 comprises a portion of the silicon substrate 535 that is dry etched to form a nanostructured surface 525 comprising nanopins 540.

The apparatus 500 further includes a second mechanical structure 545 having a second rigid surface 550 opposing the first mechanical structure 510. In the embodiment shown in FIG. 5, the second rigid surface 550 also has a second nanostructured surface 552 comprising pins 554. In the particular embodiment shown, to facilitate microparticle 505 lysing, the pins 554 of the second nanostructured surface 552 are offset from the pins 540 of the nanostructured surface 525 to form a pair of interdigitated nanostructured surfaces 525, 552. The second mechanical structure 545 can also comprise a translation stage 555, having a second substrate 560 thereon, the second substrate 560 comprising the second rigid surface 550. The translation stage 555 can comprise a spring loaded device, such as that used in microscope stages or micromanipulators, to facilitate the precise movement of the second rigid surface 550 opposing the first mechanical structure 510.

As illustrated in FIG. 5, the second rigid surface 550 can cooperate with the nanostructured surface 525 such that the microscopic particle 505 is located between the nanostructured surface 525 and the second rigid surface 550. A distance 565 between the nanostructured surface 525 and the second rigid surface 550 can be adjusted to help keep the microscopic particle 505 located between these surfaces 525, 550 while using the apparatus 500. In some cases, the distance 565 is less than about twice an average diameter 570 of the microparticle 505. Alternatively, the shape of the nanostructured surface 525 and the second rigid surface 550 can be adjusted to help keep the microparticle 505 between these surfaces 525, 550. As shown in FIG. 5, both the nanostructured surface 525 and the second rigid surface 550 can have a planar shape and be parallel to each other. In other cases, however, the nanostructured surface 525 has a convex shape and the second rigid surface 550 has a concave shape. As noted above, other combinations of shaped surfaces are also within the scope of the present invention.

Referring now to FIG. 6, illustrated is the apparatus 500 after applying a force to the microscopic particle 505 using the nanostructured surface 525 and the second rigid surface 550. For the particular embodiment of the method illustrated in FIG. 6, the force is a contact force generated when the first and second rigid surfaces 515, 550 are moved towards each other. For instance, the second rigid surface 550 is moved towards the nanostructured surface 525 to produce a contact force sufficient to rupture the microscopic particle 505, for example, by lysing its surrounding membrane or coating 605.

It will be readily apparent from the above discussion that other types of forces can be applied to the microparticle 505. The force can comprise an electric field or current generated when a voltage is applied across the nanostructured surface 525 and the second rigid surface 550. Additionally, the force can comprise an ultrasonic wave when an acoustic force is applied to one or both of the first or second rigid surfaces 515, 550.

Yet another embodiment of the present invention is a method of manufacturing an apparatus. FIGS. 7-10 illustrate cross-sectional views of an exemplary method of manufacturing an apparatus 700 according to the principles of the present invention. Any of the above-discussed embodiments of the apparatus shown in FIG. 1-6 can be incorporated into the method of manufacture.

Figure 7:
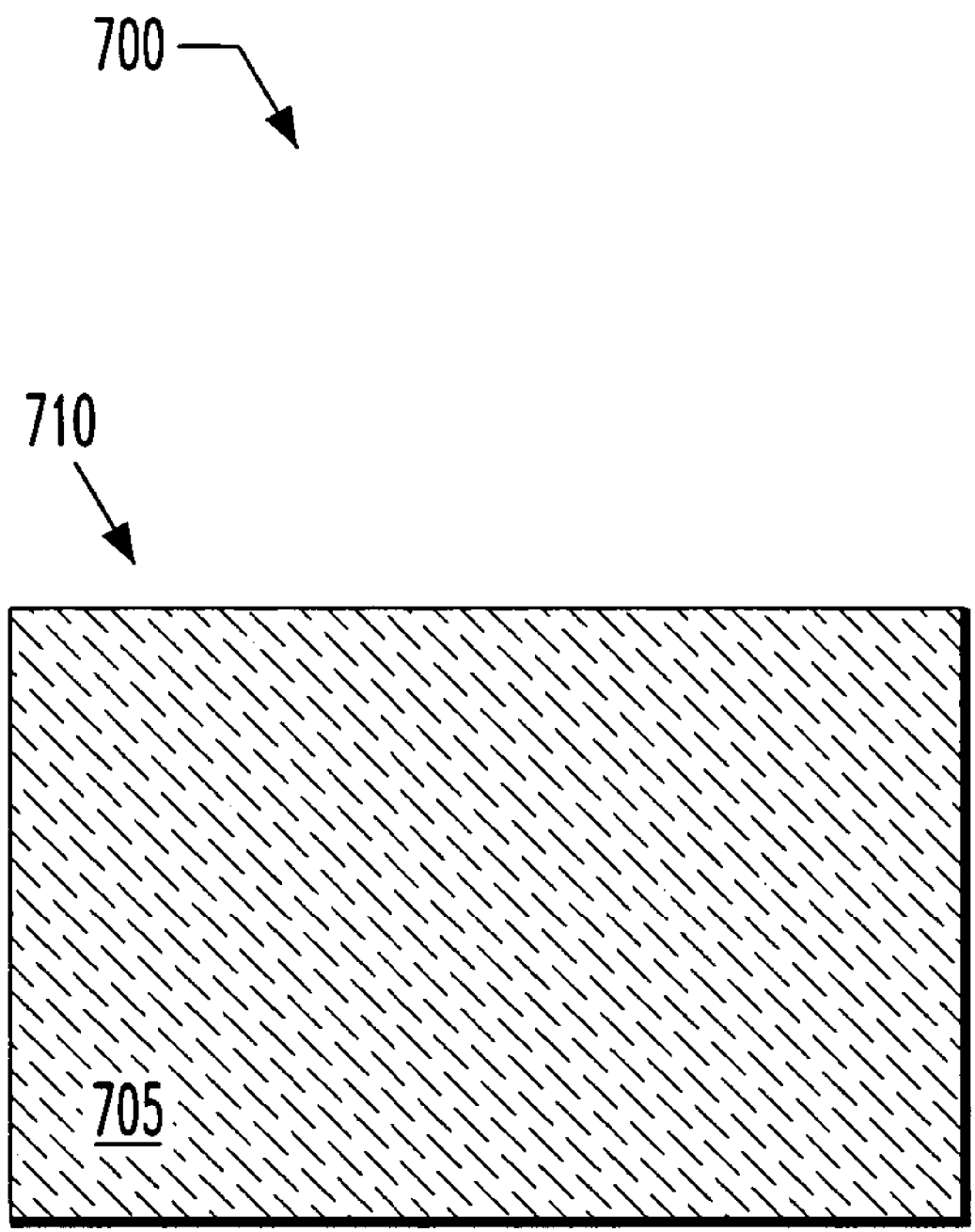
FIGS. 7-10 illustrate cross-sectional views of an exemplary method of manufacturing an apparatus according to the principles of the present invention.

Turning now to FIG. 7, illustrated is the partially constructed apparatus 700 after forming a first mechanical structure 705 having a first rigid surface 710. In some cases, the first mechanical structure 705 comprises a semiconductor substrate, such as a silicon wafer, and in some cases include a surface material offering increased mechanical rigidity, e.g., a $SiO_2$ layer, a silicon nitride layer, or an electroplated metal layer.

Figure 8:
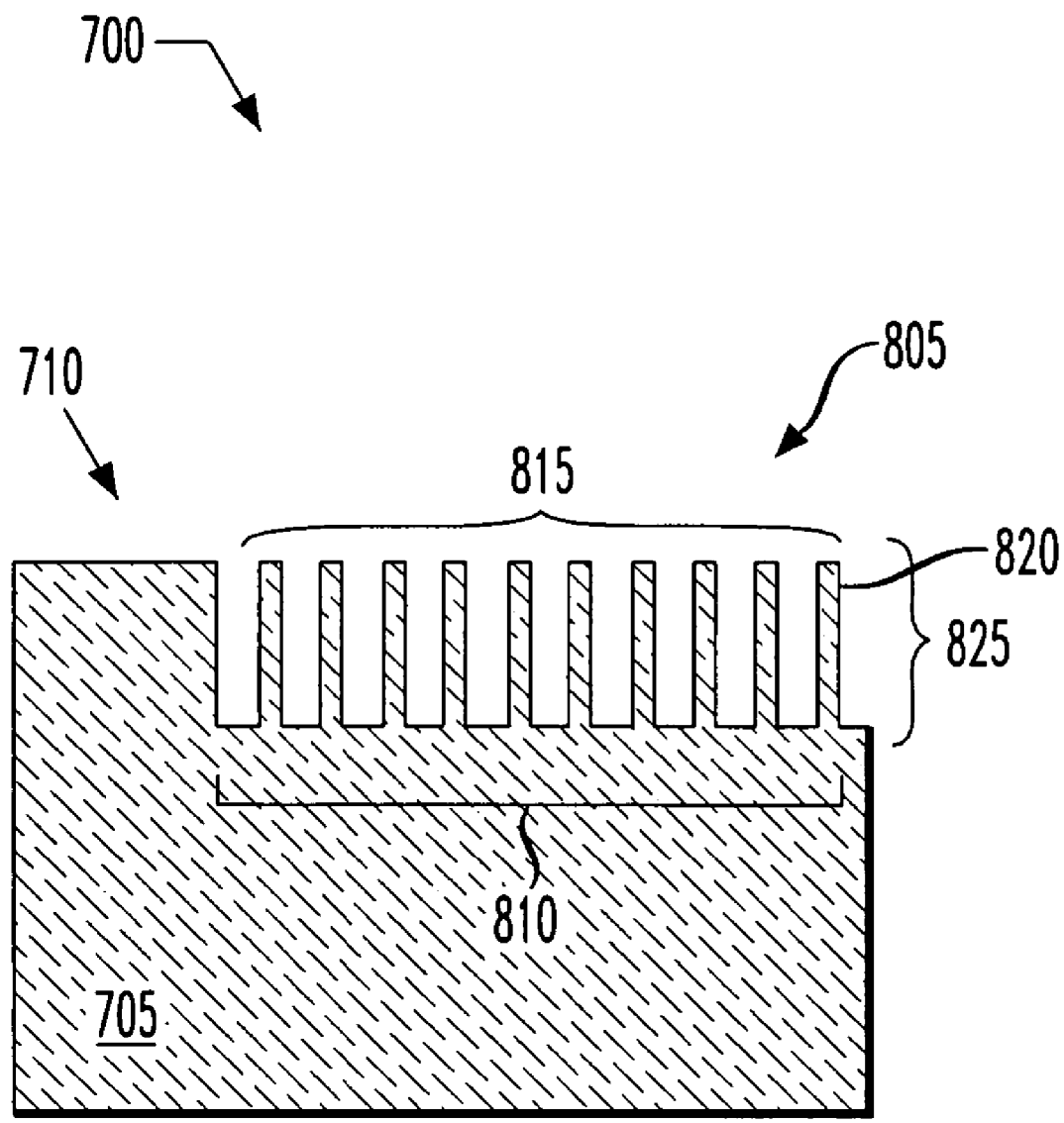

Referring now to FIG. 8, shown is the partially constructed apparatus 700 after forming a nanostructure 805 in an area 810 of the first rigid surface 710. As shown, the nanostructure 805 can comprise a surface 815 having pins 820, which in this case, form nanograss 825. The pins 820 can be formed using conventional photolithographic and dry etching procedures, for example, to remove portions of the first mechanical structure 705. Alternatively, the nanostructure 805 can be formed by patterning the surface 815 with a photoresist, electroplating a metal such as nickel over the pattern, and removing the photoresist. Other conventional methods of forming the nanostructure 805 would be readily apparent to one of ordinary skill in the art.

Figure 9:
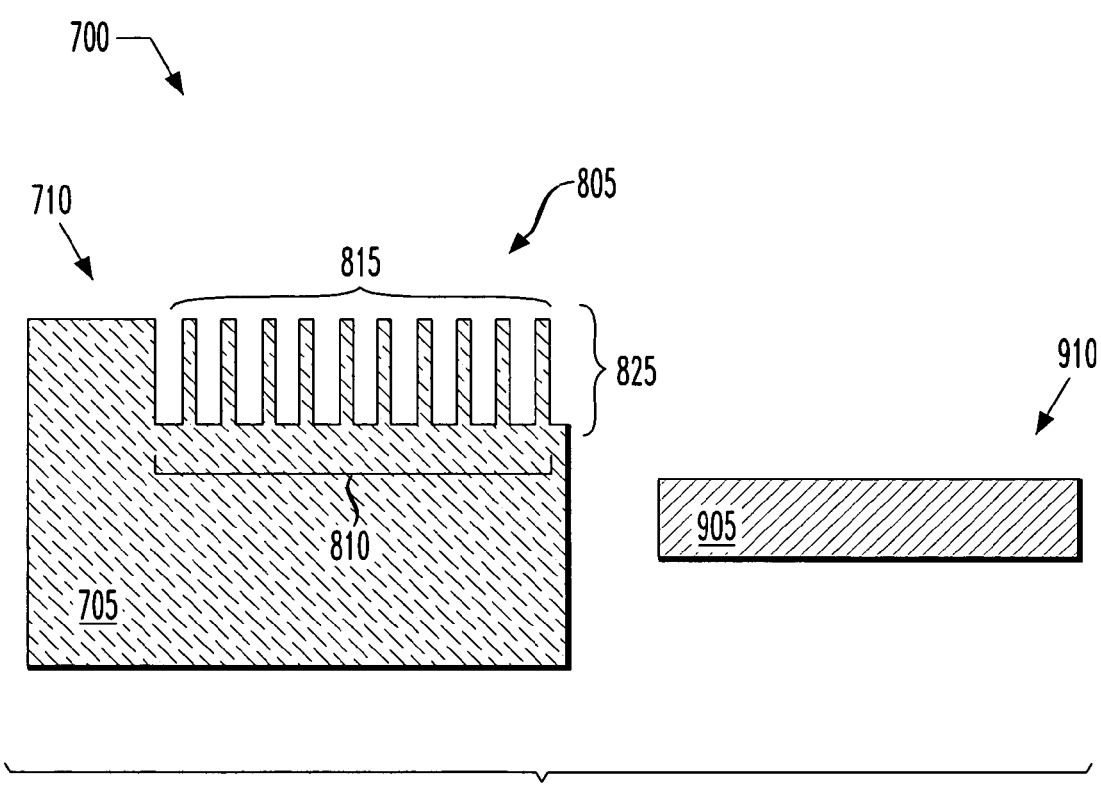

FIG. 9 depicts the partially constructed apparatus 700 after forming a second mechanical structure 905 having a second rigid surface 910. In some instances, the second mechanical structure 905 comprises a second semiconductor substrate such as a silicon wafer. In some cases, as shown, the second rigid surface 910 is planar, although in other cases a portion of the second rigid surface 910 is patterned to form a nanostructure that can be the same or different than the nanostructure 805 of the first rigid surface 710.

Figure 10:
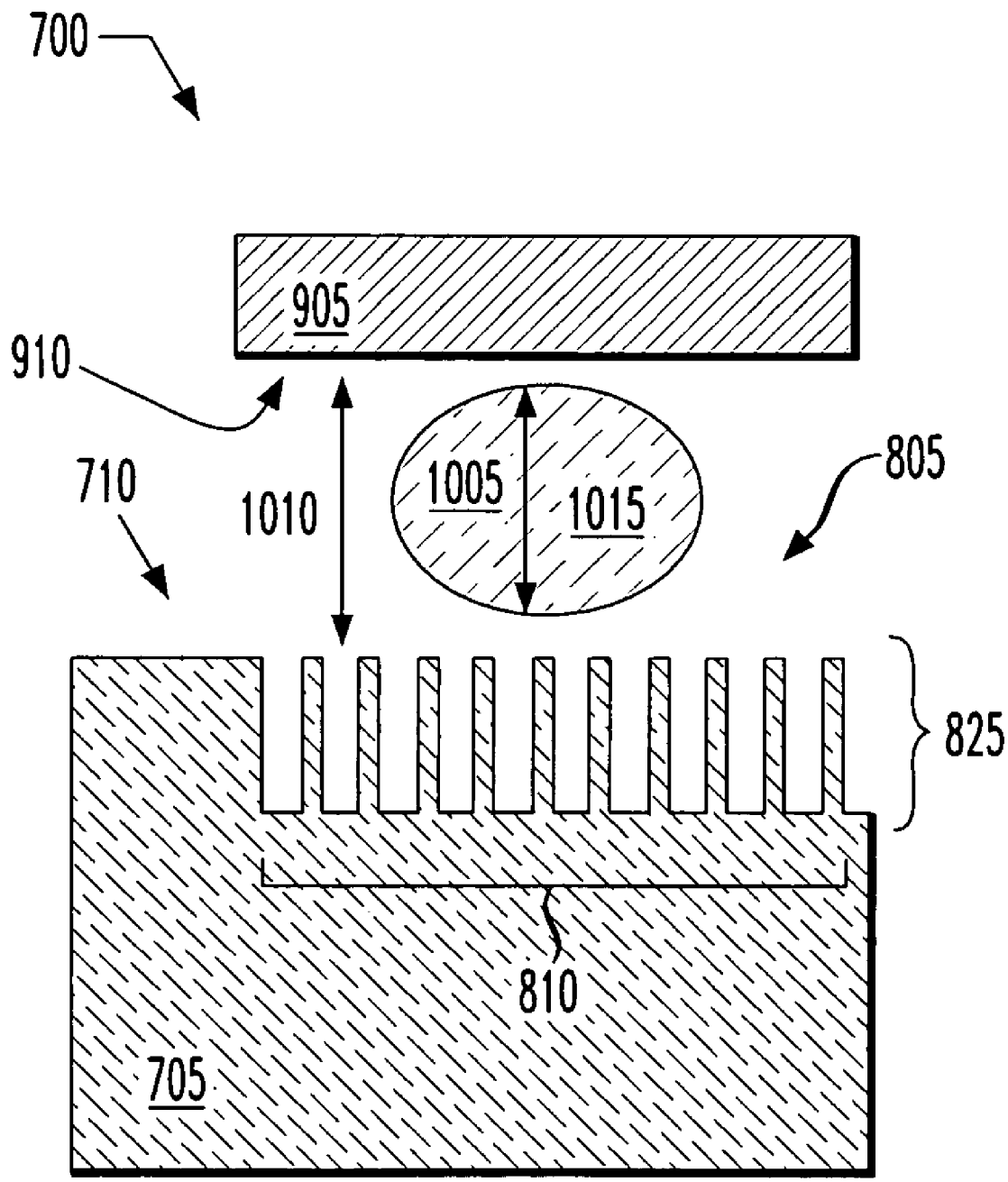

As further illustrated in FIG. 10, the second mechanical structure 905 is positioned to oppose the first mechanical structure 705. The second mechanical structure 905 is cooperable with the nanostructure 805 such that a microscopic particle 1005 is locatable between the nanostructure 805 and the second rigid surface 910. For instance, positioning can include adjusting a distance 1010 between the nanostructure 805 and the second rigid surface 910 to be less than about 2 times an average diameter 1015 of the microparticle 1005.

Although the present invention has been described in detail, those of ordinary skill in the art should understand that they can make various changes, substitutions and alterations herein without departing from the scope of the invention.

What is claimed is:

1. An apparatus, comprising:
a first mechanical structure having a first rigid surface, an area of said first rigid surface having a nano structured surface; and
a second mechanical structure having a second rigid surface and opposing said first mechanical structure and cooperable with said nanostructured surface such that a microscopic particle is locatable between said nanostructured surface and said second rigid surface, and wherein:
one of said rigid surfaces is movable with respect to the other of said rigid surfaces and cooperable to apply a contact force to said microscopic particle through said nanostructured surface,
said nanostructured surface comprises pins having a conductive core, said conductive core and said second rigid surface configured to be electrically coupled to a voltage, and
said area of said first rigid surface includes openings between said pins to form a permeable membrane.

2. The apparatus of claim 1, wherein said nanostructured surface comprises pins configured to have a pitch equal to smaller than about one-half of an average diameter of said locatable microscopic particle.

3. The apparatus of claim 1, wherein said second rigid surface further comprises openings to form a second permeable membrane.

4. The apparatus of claim 1, wherein:
said conductive core of each of said pins is insulated.

5. The apparatus of claim 1, further comprising a device configured to generate an acoustic wave applied to at least one of said first rigid surface or said second rigid surface.

6. The apparatus of claim 1, wherein said nanostructured surface comprises a plurality of blades having a diameter configured to rupture a membrane of said locatable microparticle.

7. The apparatus of claim 1, further comprising a system configured to analyze material released from said locatable microparticle when said microparticle is ruptured.

8. The apparatus of claim 1, further comprises a device configured to pass analyzed material released from said microparticle through said openings.

9. The apparatus of claim 1, wherein said microparticle is located between said nanostructured surface and said second rigid surface.

10. The apparatus of claim 9, wherein said microparticle is a biological cell.

11. The apparatus of claim 9, wherein said microparticle is a nonbiological particle.

12. The apparatus of claim 9, wherein said contact force lyses a membrane or a coating of said microparticle.

13. The apparatus of claim 1, wherein said second rigid surface further includes a second nanostructured surface.

14. The apparatus of claim 13, wherein pins of said second nanostructured surface are offset from pins of said nanostructured surface.

15. The apparatus of claim 1, wherein said nanostructured surface has a one of a convex or concave shape and said second rigid surface has the other of said convex or concave shape.

16. The apparatus of claim 1, further comprising:
a system configured to analyze material released from ruptured ones of said microscopic particles;
a microfluidic channel that directs said material to said system; and
a device configured to pass said material through openings in one or both of said first or second rigid surfaces to said system.

17. The apparatus of claim 1, further comprising:
a system configured to analyze a physical property of said microparticle in response to said contact force being applied.

18. The apparatus of claim 17, wherein said physical property is one or more of an elastic property or compressibility of said microparticle, assessed by applying said contact force between said microparticle and pins of said nanostructured surface.

19. The apparatus of claim 17, wherein pins of said nanostructured surface have tip diameters that are substantially equal to pin diameters.

20. The apparatus of claim 17, wherein said physical property is one or more of a capacitance, impedance or conductance of said microparticle, assessed by applying a voltage potential between said microparticle and conductive pins of said nanostructured surface.

21. The apparatus of claim 20, wherein said voltage potential is less than about 0.1 Volts.

22. The apparatus of claim 17, wherein said physical property is one or more of a dielectric property of said microparticle, assessed by resistance or a conductance between said microparticle and insulated conductive pins of said nanostructured surface.

23. The apparatus of claim 17, wherein said physical property is an acoustic impedance of said microparticle, assessed by applying an acoustic wave between said microparticle and said nano structured surface.

24. The apparatus of claim 17, wherein said apparatus is configured to apply to said microparticle, acoustic waves of a wavelength substantially equal to a lateral spacing between pins of said nanostructured surface.

25. The apparatus of claim 1, further including said voltage source, wherein said conductive core and said second rigid surface are electrically coupled to said voltage source.

* * * * *

UNITED STATES PATENT AND TRADEMARK OFFICE
CERTIFICATE OF CORRECTION

PATENT NO. : 7,608,446 B2
APPLICATION NO. : 10/954552
DATED : October 27, 2009
INVENTOR(S) : Aizenberg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this

Twelfth Day of October, 2010

David J. Kappos
*Director of the United States Patent and Trademark Office*